(12) United States Patent
Lee et al.

(10) Patent No.: US 7,534,456 B2
(45) Date of Patent: May 19, 2009

(54) *AGASTACHE RUGOSA* EXTRACT AND COMPOSITION CONTAINING TILIANIN ISOLATED AND PURIFIED FROM SAID EXTRACT HAVING ANTI-INFLAMMATORY ACTIVITY AND ANTI-ATHEROGENIC ACTIVITY

(75) Inventors: Hyeong Kyu Lee, Daejeon (KR); Sei Ryang Oh, Daejeon (KR); Kyung Seop Ahn, Daejeon (KR); Soon Ja Choi, Daejeon (KR); Jung Hee Kim, Gongju-si (KR); Goo Taeg Oh, Daejeon (KR); Jung Joo Hong, Seoul (KR); Seong Kyu Park, Gongju-si (KR); Woo Namkung, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 49 days.

(21) Appl. No.: 11/802,527

(22) Filed: May 23, 2007

(65) Prior Publication Data
US 2008/0081081 A1 Apr. 3, 2008

Related U.S. Application Data

(62) Division of application No. 10/469,025, filed as application No. PCT/KR01/02224 on Dec. 20, 2001, now abandoned.

(30) Foreign Application Priority Data

Feb. 27, 2001 (KR) .................................. 2001-9977

(51) Int. Cl.
*A01N 65/00* (2006.01)
(52) U.S. Cl. ..................................................... 424/725
(58) Field of Classification Search ........................ None
See application file for complete search history.

(56) References Cited

U.S. PATENT DOCUMENTS 5,776,462 A 7/1998 Tsai et al.
2002/0025348 A1* 2/2002 Basu et al. .................. 424/735

FOREIGN PATENT DOCUMENTS

KR 2002-0012435 A 2/2002

OTHER PUBLICATIONS

Zakharova et al., Flavanoids of Agastache rugosa, 1980.*
Chong et al., "Current, New and Future Treatments in Dyslipidaemia and Atherosclerosis," Drugs 60(1):55-93 (2000).
Hayashi et al., "Inhibition of Cow's Milk Xanthine Oxidase by Flavonoids," J. Nat. Prod. 51(2):345-348 (1988).
Hong et al., "Inhibition of Cytokine-induced Vascular Cell Adhesion Molecule-1 Expression; Possible Mechanism for Anti-atherogenic Effect of *Agastache rugosa*," FEBS Letters 495(3):142-147 (2001).
International Preliminary Examination Report of PCT/KR01/02224 (Jul. 17, 2003).
International Search Report of PCT/KR01/02224 (Apr. 25, 2002).
Kim et al., "HIV Integrase Inhibitory Activity of *Agastache rugosa*," Arch. Pharm. Res. 22(5):520-523 (1999).
Kirschfink, "Controlling the Complement System in Inflammation," Immunopharmacology 38(1-2):51-62 (1997).
Lee et al., "Agastaquinone, a New Cytotoxic Diterpenoid Quinone from *Agastache rugosa*," J. Nat. Prod. 58(11):1718-1721 (1995).
Mohri et al., "Coronary Microvascular Disease in Humans," Jpn. Heart J. 40(2):97-108 (1999).
Oh et al., "In Vitro Anticomplementary Activity of Phenylpropanoids from *Agastache rugosa*," Kor. J. Pharmacogn 27(1):20-25 (1996).
Rothlein et al., "Treatment of Inflammation with anti-ICAM-1," Res. Immunol. 144(9):735-739 (1993).
Zou et al., "Studies on the Chemical Constituents from Roots of *Agastache rugosa*," Yao Xue Xue Bao 26(12):906-910 (1991).

* cited by examiner

*Primary Examiner*—Michael V Meller
(74) *Attorney, Agent, or Firm*—Finnegan, Henderson, Farabow, Garrett & Dunner LLP

(57) ABSTRACT

This invention includes a composition of *Agastache rugosa* and tilianin obtained by separation-purification for anti-inflammation and anti-atherosclerosis, and more particularly, an extract of *Agastache rugosa* and tilianin obtained therefrom by separation-purification which are effective in preventing and treating not only inflammatory diseases but also atherosclerosis related to inflammatory responses and disease in the circulatory system caused by atherosclerosis because they are excellent in inhibiting the activity of complement systems as a factor of inflammatory responses, the expression of intercellular adhesion molecule-1 (ICAM-1) and vascular cell adhesion molecular-1 (VCAM-1), and the production of nitric oxide (NO). They can also significantly reduce the development of atherosclerosis due to the inflammatory response.

14 Claims, 2 Drawing Sheets tissue of lesions under vascular endothelial cells
(red region)

A (Control)        B (1% *A.rucosa* treatment)

red region : macrophage accumulated region

A (Control)        B (1% *A.rucosa* treatment)

AGASTACHE RUGOSA EXTRACT AND COMPOSITION CONTAINING TILIANIN ISOLATED AND PURIFIED FROM SAID EXTRACT HAVING ANTI-INFLAMMATORY ACTIVITY AND ANTI-ATHEROGENIC ACTIVITY

This is a divisional of application Ser. No. 10/469,025, submitted under 35 U.S.C. § 371 on Aug. 26, 2003 now abandoned, which is a national stage application of PCT/KR01/02224, filed on Dec. 20, 2001, and is based upon and claims the benefit of priority from the prior Korean Patent Application No. 2001-9977, filed Feb. 27, 2001, all of which are incorporated herein by reference.

FIELD OF THE INVENTION

The present invention relates to a composition comprising *Agastache rugosa* and tilianin obtained therefrom by separation-purification for anti-inflammation and anti-atherosclerosis, and more particularly, to an extract of *Agastache rugosa* and tilianin obtained therefrom by separation-purification which is effective in preventing and treating not only inflammatory diseases but also atherosclerosis related to inflammatory responses and disease in circulatory system caused by atherosclerosis because they are excellent in inhibiting the activity of complement system as a factor of inflammatory responses, the expression of intercellular adhesion molecule-1 (ICAM-1) and vascular cell adhesion molecular-1 (VCAM-1), and the production of nitric oxide (NO). They can also significantly reduce the development of atherosclerosis due to inflammatory responses.

BACKGROUND OF THE INVENTION

When there is a damage in a tissue or a cell or an infection by a foreign substance in a human body (e.g., bacteria, molds, virus, various allergy-inducing materials), it usually entails an inflammatory response expressed as a series of complex physiological responses such as activation of enzyme, secretion of inflammation-mediating materials, infiltration of body fluid, cell movement, and damage of tissues that are related to all sorts of inflammation-mediating factors and immunocytes in local blood vessels, body fluid, and as external symptoms such as erythema, edema, and pyrexia. Normally, inflammatory responses remove external sources of infection, reproduce damaged tissues, and recover the function of life, but when an antigen is not removed or inflammatory responses occur excessively or continuously due to intrinsic substances, inflammatory responses become the main pathological symptoms of diseases (hypersensitive disease, chronic inflammation) and the main obstacles in the processes of treatment such as blood transfusion, drug administration and organ transplantation, and the like.

The effects of factors involved in inflammatory responses relating to the present invention are described as follows.

Complement system is a major factor of body fluid, which activates and amplifies inflammation at the early stage of an immune response. Active proteins (anaphylatoxins; C3a, C4a, C5a) and conjugated proteins (membrane attack complex (MAC)) produced in the activation process of complement system are related to various inflammatory diseases (rheumatic arthritis, lupus erythematosus, adult respiratory distress syndrome, Alzheimer's disease) and often become the direct causes of superacute rejections in organ transplantation.

ICAM-1 is a typical protein of cell adhesion molecule group expressed on the surface of endothelial cells. Normally, it is expressed in a very low level, however, when it is stimulated by inflammation-mediating molecules of cytokines such as TNF-$\alpha$, interferon-$\gamma$, and interleukin-1$\beta$, the level of expression is accelerated rapidly to play a role in adhering inflammatory cells such as monocytes or lymphocytes that move in blood and in moving the inflammatory cells to the inflammatory tissues. Therefore, the expression of ICAM-1. plays an important rote in the amplification of inflammation when inflammatory cells move and gather on the inflammatory tissues at its early stage.

VCAM-1 is one of cell adhesion molecule groups expressed on the surface of endothelial cells. The expression increases rapidly in the endothelial cells of blood vessels when atherosclerotic lesions are produced in the animal model (apolipoprotein-E-deficient mice, ApoE–/–) analogous with the progress of human atherosclerosis. And the increase of VCAM-1 expression is directly correlated with the concentration of cholesterol—low density lipoprotein (cholesterol-LDL) in the plasma. Therefore, when atherosclerotic lesions are induced, VCAM-1 expressed in the endothelial cells of blood vessels adheres monocytes/and lymphocytes in the blood and those inflammatory cells gather under endothelial cells of blood vessels, thus playing an important role in development of atherosclerotic lesions.

NO is produced together with L-citrulline after L-arginine is oxidized by nitric oxide synthase (NOS). NO is a mediating-molecule concerned with vasodepression, adhesion and coagulation of blood platelets, neurotransmission, movement of digestive organism, and erection of penis by affecting the blood vessel system. And NO protects against a microbial infection by being produced not only in inflammatory cells but also in nonimmune cells. Meanwhile, the inducible-NOS (iNOS), one of NOS participating in producing NO is independent of calcium or calmodulin and expressed by stimulation of lipopolysaccharide (LPS) and cytokines (IFN-$\gamma$, TNF and the like). Because cyclooxygenase-2 (COX-2) is also activated by this stimulation thereby producing inflammation-mediating molecules, prostaglandins, there is close correlation between the expression of iNOS and COX-2, and thus produced NO also affects the expression of COX-2. Production of NO in macrophages is selectively induced by the expression of iNOS, and thus induces activation of other inflammatory responses. Therefore, NO is an important factor of inflammatory diseases.

Atherosclerosis is a disease with arteries becoming hardened caused by genetic conditions related to lipid metabolism and environmental conditions such as eating habits, smoking and lack of exercise, and it can result in diseases of circulatory system such as a heart disease and a vascular disease of brain. A hypothesis about early outbreak of atherosclerosis is "response-to-injury" hypothesis and this means that the endothelial cells of blood vessels become dysfunctioned by being unable to maintain normal homeostasis as the result of genetic changes, peroxides, hypertension, glycosuria, increase in plasma homocysteine concentration and microbial infection, and the like. When the endothelial cells of blood vessels become dysfunctioned, the expression of cell adhesion molecules becomes high, cell transmission increases, and then adhesion of immunocytes, platelets and fat, and transmission to the tissue begin to increase. Inflammatory responses such as secretion of an inflammation-mediating factor and a growth factor of the immunocyte result in generation of atherosclerotic lesions. Wherein, as a result of oxidation, saccharide bonding, accumulation and glycoprotein bonding, low-density lipoprotein (LDL) in blood becomes modified-LDL (MLDL), which induces stimuli and damage of the endothelial cells of blood vessels and smooth muscles. On this account, when the expression of VCAM-1 on the endothelial cells and release of inflammation-mediating factor of inflammatory cells are promoted, LDL is flowed and accumulated under the endothelial cells, and accumulated LDL and oxidized MLDL repeat the process of inducing inflow and activation of immunocytes such as macrophages, T-lymphocyte and the like, and consequently inflammation of lesion is promoted. Thereafter, the speck is necrotized by macrophage inflowed to the lesion, and hydrolase released from lymphocyte, inflammation-mediating factor and growth factor. Through the repeating processes of inflow of monocytes to the region of the necrotized focus, movement and differentiation of smooth muscle, as well as formation of fibrous tissues, lesion tissue grows into a complex structure of fibrous tissues covered with fibroid materials in necrotic tissue having MLDL as a core part. Thrombus is produced from the grown lesion tissue, arteries become hardened and diseases of circulatory system such as hindrance of blood flow occur. Therefore, atherosclerosis occurs when the amount of fat such as cholesterol and LDL in the blood is high, but it does not occur simply by accumulation of fat. Rather, atherosclerosis is a typical inflammatory response that endothelial cells, macrophages and lymphocytes correlate with a series of process of inflow and accumulation of fat under the endothelial cells of arteries, progress of lesion thereafter and finally cell necrosis.

Agastache rucosa is a perennial plant, which belongs to Labiatae family and is distributed in Northeast Asia that includes Korea, Japan, China, and etc. In Korea, it mostly grows wild in southern area or cultivated in some areas. In Chinese medicine, the aerial part of this plant is called Patcholi (other name of Agastache rugosa) and a Chinese book, "Myoneubyolok", says "it removes bad energy from our body and toxin by configuration of the ground, and cures cholera morbus, that is, cures one's sickness inside and intestinal convulsion". Among the ordinary people, the leaf is used as a savor material in various soups such as loach soup and the flower is used as a honey source.

The study on components of Agastache rugosa reports that there are kinds of essential oil, sesquiterpene, diterpene, triterpene, flavonoid, phenylpropanoid and carotenoid. The study on physiological activity of Agastache rugosa reports antibacterial activity of the extract [Phytother. Res. 14(3), 210-212, 2000; J. Food Sci. Nutr. 4(2), 97-102, 1999], antiviral activity [Arch. Pharm. Res. 22(5), 520-523, 1999; U.S. Pat. No. 5,776,462], and inhibitory activity against monoamine oxydase [The Pharmaceutical Society of Korea 42(6), 634-638, 1998]. And also, antibacterial [Zhongguo Yaozue Zazhi 35(1), 9-11, 2000; Weishengwuxue Zazhi 18(4), 1-4, 16, 1998] and mosquito avoidance activity of essential oil [Chinese Pat. No. 1044205], anticancer activity of carotenoid [The Korean Society of Pharmacognosy 30(4), 404-408, 1999], anticancer [J. Nat. Prod. 58(11) 1718-1821, 1995] and antiviral activity of diterpene [Arch. Pharm. Res. 22(1), 75-77, 1999], and antiviral activity of phenylpropanoid [Arch. Pharm. Res. 22(5), 520-523, 1999], anti-oxidation [The Korean Society of Agricultural Chemistry and Biotechnology 42(3), 262-266, 1999] and anti-complement activity [The Korean Society of Pharmacognosy 27(1), 20-25, 1996; The Korean Society of Agricultural Chemistry and Biotechnology 39(2), 147-152, 1996] have been reported. However, there is no report of study yet on anti-inflammatory and anti-atherosclerotic activity of extract of Agastach rugosa neither at home nor abroad.

Tilianin, on the other hand, has been reported to be present in various plants as glucose-glycoside compound of acacetin, one of flavonoids.

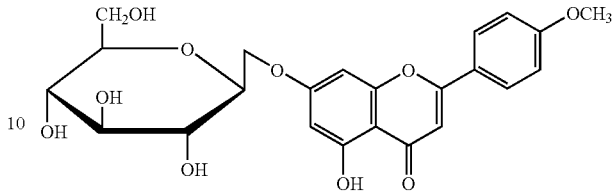

The study on physiological activity of tilianin reports anti-oxidation activity [J. Food Sci. Nutr. 4(1999), 221-225; Indian J. Chem., Sect. B: Org. Chem. Incl. Med. Chem 36B (1997), 1201-1203] and no inhibitory activity of xanthine oxidase [J. Nat. Prod. 51(1988), 345-348]. But, there is no report of the study yet on anti-inflammatory and anti-atherosclerotic activity of tilianin neither at home nor abroad.

SUMMARY OF THE INVENTION

Hence, the inventors investigated anti-inflammatory and anti-atherosclerotic activity of drugs of natural origin used for food and medicinal purposes in order to select natural drugs that do not hinder normal lipid metabolism and are able to control the progress of atherosclerotic lesions caused by anti-inflammatory activity. As a result, the present invention completed by finding that extract of Agastache rucosa has inhibitory activity against various inflammatory factors and excellent anti-atherosclerotic activity decreasing significantly atherosclerotic lesions related to inflammatory responses.

The object of the present invention is, therefore, to provide an extract of Agastache rugosa and tilianin obtained therefrom by separation-purification which is effective as drugs and food additives for preventing as well as treating inflammatory diseases, atherosclerosis which is related to inflammatory responses and diseases of circulatory system due to atherosclerosis because theft have an anti-inflammatory activity and an anti-atherosclerotic activity.

DETAILED DESCRIPTION OF THE INVENTION

Figure 1:
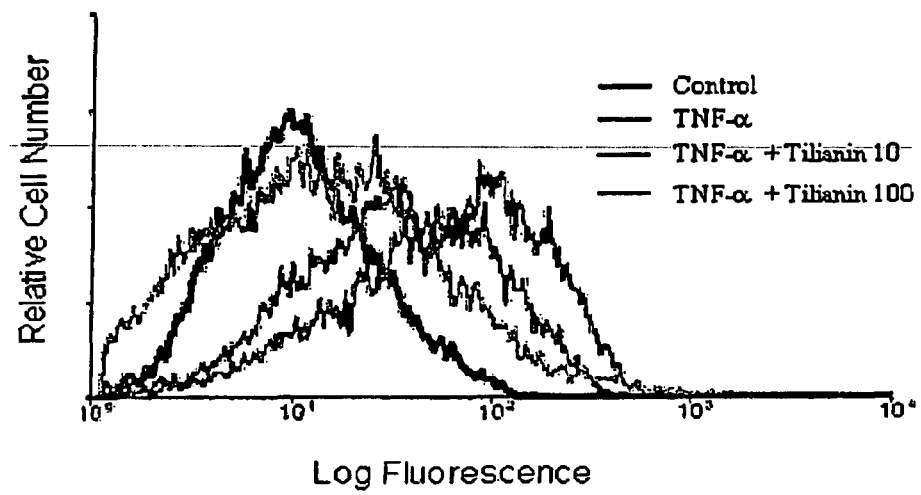
FIG. 1 shows dose-dependent effect of tilianin on endothelial molecule induction. HUVECs were preincubated with 10 or 100 μM tilianin for 2 hours and stimulated with TNF-α (10 ng/ml) for 16 hours, stained for VCAM-1 or isotype control, and analyzed by flow cytometry.

The present invention relates to a composition, which has an anti-inflammatory and anti-atherosclerotic activity comprising an extract of *Agastache rugosa* and tilianin obtained therefrom by separation-purification as an active ingredient.

The present invention is described in more detail as follows.

The extract of *Agastache rugosa* or tilianin obtained by separation-purification, according to the present invention, has an inhibitory activity of inflammatory factors, i.e. an anti-complement activity, an inhibitory activity against the expression of ICAM-1 and VCAM-1, and an inhibitory activity against the production of NO, so it is effective for prevention and treatment of not only inflammatory diseases but also atherosclerosis due to its excellent inhibitory activity against atherosclerotic lesion related to inflammatory responses.

Therefore, the present invention includes drugs or food additives comprising an extract of *Agastache rugosa* and tilianin obtained by separation-purification as an active ingredient.

The process of separation-purification of extracts of *Agastache rugosa* and tilianin, according to the present invention, is described in more detail below.

The extract of *Agastache rugosa* is obtained by drying whole plant of *Agastache rugosa*, extracting it with low-grade alcohol followed by it concentration. Fractional yield of the extract is about 10 to 20% of weight of dried *Agastache rugosa*. Thus obtained extract of *Agastache rugosa* is suspended in water, fractionated by n-hexane of the same volume after sufficient shaking and fractionated by chloroform and low grade alcohol added in this order, and then the fractions by solvent are obtained. Here, low-grade alcohol is alkyl-alcohol of 1 or 6 carbons, desirably n-butanol. The fraction method by solvent is subject to conventional method such as column chromatography with silica gel and high-speed liquid chromatography. Or general separation-purification method such as recrystallization can be used.

Anti-complement activity against complement system, inhibitory activity against ICAM-1 expression, inhibitory activity against VCAM-1 expression and inhibitory activity against NO production, and anti-inflammatory activity and inhibitory activity of atherosclerotic lesion in mice with carrageenan induced-acute inflammation were examined respectively in the extract of *Agastache rugosa* obtained as above-mentioned and tilianin obtained by separation-purification.

The extract of *Agastache rugosa* has anti-complement activity which strongly inhibits complement activation of human serum against immune complex. And, it inhibits strongly expression of ICAM-1 against THP-1 monocytic leukemic cells (THP-1 cells) which induce ICAM-1 expression by tumor necrosis factor-α (TNF-α). And, it has a strong inhibitory activity against NO production of mice's monocyte/macrophage RAW264.7 cells which were activated by lipopolysaccharide (LPS). Also, it shows strong anti-inflammatory activity in mice with carrageenan induced-acute inflammation and when low-density lipoprotein receptors-deficient mice (LDLR−/−mice) are bred with 1% of extract of *Agastache rugosa* added to the feed, atherosclerotic lesion decreased remarkably in aortic sinus of the control group.

Moreover, it was confirmed that the hexane fraction of extract of *Agastache rugosa* has strong anti-complement activity as described above and inhibitory activity against ICAM-1, expression, the chloroform fraction has strong inhibitory activity against ICAM-1 expression and inhibitory activity against NO production, and the butanol fraction has strong inhibitory activity against ICAM-1 expression.

Meanwhile, the method of preparing drugs and food additives accords with a well-known method because the present invention includes drugs and food additives comprising extract of *Agastache rugosa* and tilianin obtained by separation-purification as an active ingredient.

The extract of *Agastache rugosa* and tilianin can be used in themselves because they are natural form but they can also be made into powder, granule, capsule or injection mixed with carriers, forming agents, and diluents that are permitted pharmaceutically. Also the extract of *Agastache rugosa* has been used for foods and drugs from the old times and the dosage is not limited and can be varied according to internal absorbency, weight, patient's age, sex, health condition, administration time, administration method, excretion ratio, and degree of disease. Generally, the desirable amount of the extract of *Agastache rugosa* (concentrated state) and tilianin as an active ingredient is 0.1~100 mg/kg (weight). Therefore, the composition comprising active ingredients of the present invention must be prepared in consideration of limits of significant dosage and specialized administration is used or carried out several times with intervals upon necessity such as decision of an observer or an expert and requirement of each individual.

Meanwhile, when the extract of *Agastache rugosa* and tilianin are prepared as food additives, they can be included in food stuff such as drinks, gums, pastries, etc.

Drugs and food additives comprising the extract of *Agastache rugosa* and tilianin as active ingredients as described above are excellent in preventing and curing inflammatory diseases, atherosclerosis, and diseases of circulatory system due to atherosclerosis.

The present invention is explained in detail hereinbelow using the following examples, however, the scope of the present invention shall not be limited by the following examples.

PREPARATION EXAMPLE 1

Preparation of the Extract from *Agastache rugosa* and the Fraction by Solvent

After gathering, drying, and finely cutting 30 kg of the aerial part of *Agastache rugosa* cultivated in the farm, it was kept with methanol (120 L) for 3 days. And the extract (3.5 kg) was obtained by concentrating the extract (30 kg) three times. Some extract (2.5 kg) was then suspended in water (10 L) and fractionated by n-hexane (10 L) two times. As a result, 380 g n-hexane fraction was obtained. Subsequently, it was fractionated by chloroform and n-butanol as mentioned above and concentrated. As a result, 590 g of chloroform fraction, 450 g of n-butanol fraction, and 980 g of water fraction were obtained.

PREPARATION EXAMPLE 2

Separation-purification of Tilianin from *Agastache rugosa*

Thirty kg of material was obtained after gathering, drying and cutting finely the aerial part of *Agastache rugosa* cultivated in the farm. It was kept with methanol (120 L) for 3 days and the extract (3.5 kg) was obtained by extracting it (30 kg) 3 times.

Some (2.5 kg) of the extract was then suspended in water (10 L), fractionated by chloroform (10 L) and by repeating the procedure two times, chloroform fraction was removed. Subsequently, it was fractionated with n-butanol as above-mentioned method and 450 g of n-butanol fraction was obtained. The n-butanol fraction (150 g) adsorbed to silica gel (1 kg) was subject to column chromatography (25×75 cm) filled with silica gel (4 kg) and then the fraction comprising tilianin was eluted using a chloroform-methanol mixture (methanol ratio: 5%~10%). The remaining fraction (300 g) was kept with methanol (10 L) and the precipitate gained here was washed with methanol several times and the precipitate containing more than 90% tilianin was obtained. Pure tilianin gained by two above-mentioned methods separated from tilianin containing compound using high-speed liquid chromatography.

EXAMPLE 1

Anti-complement Activity

Measurement of anti-complement activity of complement system was carried out by modified method used by Meyer et al. [Kabat, E. A. and Mayer M. M. (1961) in "Experimental Immunochemistry" $2^{nd}$ ed. Charles and Thomas, USA] and the process of experiment is as follows.

Fresh red blood cell of sheep was washed with gelatin-veronal buffer solution (1.8 mM of sodium barbital, 3.1 mM barbital acid, 0.10% gelatin, 0.141 M of salt, 0.3% sodium azide, 0.5 mM of magnesium chloride, 0.15 mM calcium chloride, pH 7.3) three times and then set to the concentration of $5\times10^8$ cell number/ml. Antibody (anti-sheep red blood cell stroma rabbit antisera, S-1389, Sigma) was diluted to 1/100 in the above-mentioned buffer solution, mixed with the diluted solution of sheep blood cell by the same volume, stirred slowly in 37° C. incubator for 1 hour and sensitized erythrocytes (EA) was prepared, which was washed two times with cold buffer solution with concentration set to $5\times10^8$ cell number/ml. Complement (serum) gained from human blood after centrifugation at 2500×g was diluted to 1/90 in a buffer solution, mixed with 40 μl of EA solution, 80 μl of diluted solution of complement and 80 μl of buffer solution, and put in a 37° C. incubator for reaction. And then absorbance was immediately measured at 504 nm for 100 μl of upper solution after centrifugation. Absorbance of each antibody and complement (serum) according to concentration was measured, and diluted concentration of antibody and serum (complement) for outbreak of 50% hemolysis (standard hemolysis) was determined. Subsequently, samples for test melted in DMSO were diluted in 80 μl of a buffer solution to 2.5% which was added for standard hemolysis and then measurement of absorbance was repeated three times, and decrease of absorbance was calculated. Then using this, inhibitory activity against hemolysis of samples for test was converted into anti-complement activity.

$$\text{Hemolysis Index (\%)} = \frac{\text{hemolysis absorbance of sample group} - \text{absorbance of sample only}}{\text{maximal hemolysis absorbance of reactive solution} - \text{absorbance of reactive solution only}} \times 100$$

$$\text{Activity of anti-complement (\%)} = \frac{\text{Hemolysis Index of Sample Group}}{\text{Hemolysis Index of Standard}} \times 100$$

As a result, the n-hexane fraction and chloroform fraction of the extract of *Agastache rugosa* showed high anti-complement activity as shown in Table 1.

TABLE 1

| Samples | Concentration (μl/ml) | Activity of anti-complement (%) |
|---|---|---|
| Extract of *Agastache rugosa* | 125 | 95.6 ± 1.1 |
| | 62.5 | 63.8 ± 2.0 |
| | 32 | 62.7 ± 5.4 |
| n-hexane fraction | 125 | 100.7 ± 0.2 |
| | 62.5 | 99.7 ± 0.1 |
| | 32 | 98.5 ± 0.3 |
| Chloroform fraction | 125 | 100.4 ± 1.2 |
| | 62.5 | 100.2 ± 0.1 |
| | 32 | 60.2 ± 0.9 |
| n-butanol fraction | 125 | 49.8 ± 1.1 |
| | 62.5 | 26.3 ± 2.7 |
| | 32 | 1.3 ± 1.8 |

EXAMPLE 2

Inhibitory Activity Against ICAM-1 Expression

The following is the process of experiment on inhibitory activity against ICAM-1 expression for THP-1 cells.

THP-1 cells were cultured in $CO_2$ incubator (5% $CO_2$, 95% relative humidity, 37° C.) using RPMI-1640 broth (RPMI-1640, Gibco BRL 23400-021, 1.62%; 0.2% $NaHCO_3$; 1% antimicrobial agents with penicillin and streptomycin mixed) with 10% fetal bovine serum (Gibco BRL 26140-079, FBS) added to the culture media. Samples for test were melted in DMSO, diluted with phosphate buffered saline solution (PBS) to below 5% and added to reactive solution by 5%, so as to set the concentration of DMSO with samples melted therein not to exceed 0.25% in the final solution. 200 μl of THP-1 cells ($2.5\times10^5$ cells/ml) was divided into each well of 96-well with addition of 10 μl of solution prepared at constant concentration. After culturing it in 37° C. $CO_2$ incubator for 1 hour, TNF-α (final concentration: 10 ng/ml) was added to induce ICAM-1 expression and it was cultured in $CO_2$ incubator for 16 more hours. The reactive solution was made to isolate nonspecific bonding part by adding 25 μl of glutaraldehyde buffer solution (glutaraldehyde 2.08% in PBS) to set cells at well, washing it with PBST (0.005% tween-20 in PBS) and adding 3% skim milk. After washing it again, primary antibody (anti-human ICAM-1) and secondary antibody (anti-mouse IgG peroxidase conjugate) were added in order, 200 μl of substrate solution for coloring (OPD Peroxidase substrate (Sigma P-9187), in 0.05 M phosphate-citrate buffer) was added and then 50 μl of 3 M HCl was added after 5~10 minutes to stop the reaction. Then, the inhibition ratio of the expression by samples was calculated after measuring absorbance at 490 nm and ICAM-1 expression of THP-1 cells by TNF-α.

$$\text{Value of ICAM-1 Expression} = \frac{\text{Absorbance of } TNF-\alpha \text{ group} - \text{Absorbance of nonspecific bond}}{\text{Absorbance of control group} - \text{Absorbance of nonspecific bond}}$$

$$\text{Inhibition ratio of ICAM-1 expression (\%)} = \left(1 - \frac{\text{mean value of ICAM-1 expression of sample group}}{\text{mean value of ICAM-1 expression of conrol group}}\right) \times 100$$

TABLE 2

| Sample | Concentration (μg/ml) | Inhibitory activity of ICAM-1 expression (%) |
|---|---|---|
| Extract of | 25 | 12.3 ± 2.7 |
| *Agastache rugosa* | 50 | 18.4 ± 3.2 |
| n-hexane fraction | 25 | 17.4 ± 2.3 |
|  | 50 | 41.4 ± 4.2 |
| Chloroform fraction | 25 | 12.0 ± 12.6 |
|  | 50 | 37.1 ± 1.5 |
| Butanol fraction | 25 | 13.9 ± 3.3 |
|  | 50 | 21.4 ± 4.6 |
| Tilianin | 25 | 29.8 ± 2.9 |
|  | 50 | 32.7 ± 3.7 |
| Dexamethasone* | 30 μM | 40.1 ± 1.7 |

*Positive control

As shown in Table 2, the inhibitory activity against ICAM-1 expression of the extract of *Agastache rugosa*, the solvent fraction thereof and tilianin was lower than dexamethasone, known as anti-inflammation agent, but particularly the n-hexane fraction and the chloroform fraction show excellent inhibitory activity. While dexamethasone has an excellent effect as a steroid agent, side effects (dysfunction of kidney, increase of inflammation, glycosuria, contraction of muscle, growth inhibition, osteoporosis, etc.) are found in this agent like any other steroid agents for long use. But the extract of *Agastache rugosa* and tilianin are free from these side effects.

EXAMPLE 3

Inhibitory Activity Against VCAM-1 Expression

The process of experiment on inhibitory activity against VCAM-1 expression of human umbilical vein endothelial cells (HUVECs) is as follows.

HUVECs were cultured in $CO_2$ incubator (5% $CO_2$, 95% relative humidity, 37° C.) using EGM-2 Bulletkit broth [Kit which contains a 500 ml bottle of Endothelial Cell Basal Medium-2 (EBM-2, Clonetics CC-3156, MD, USA)] with 100 U/ml of penicillin and 100 μg/ml of streptomycin added. Samples for test were melted in DMSO, concentration of which to remain below 0.1% in the final reactive solution. HUVECs were used as much as two culture dish (Ψ10 cm, $2 \times 10^6$ cells) for each group, and the broth was exchanged prior to treatment of samples. First, tilianin was pretreated with final concentration of 100 μM and 10 μM for 2 hours. Then, TNF-α was treated to become 10 ng/ml for each group and VCAM-1 expression was induced for 16 hours. After being washed with PBS two times and trypsinized (0.025%) for 5 minutes, cells were collected. After the collected cells were centrifuged in 15 ml tubes, the upper solution was removed, cell precipitates were suspended with PBS, and the cells were centrifuged again and washed. After washing cells with PBS two times, cells were suspended in 100 μl of PBS with 0.5% BSA (Bovine Serum Albumin) added and mouse anti-human monoclonal antibody (Rb 1/9; 1 μg/ml) was added. After monoclonal antibody was induced to conjugate with cells on ice for 30 minutes, cells were washed three times with cold PBS and incubated in ice with FITC (fluorescein isothiocyanate) which is conjugated with goat F(ab')2 anti-mouse IgG at a dilution of 1:25 (W/W) in PBS for 40 minutes. Cells were then fixed with 1% paraformaldehyde and analyzed by FACScan (Bio-Rad, USA) to measure inhibitory activity against VCAM-1 expression by samples for test.

$$\text{Inhibition ratio of VCAM-1 expression (\%)} = \left(1 - \frac{\text{mean value of fluorescent intensity of sample group}}{\text{mean value of fluorescent intensity of control group}}\right) \times 100$$

Shown in Table 3 and FIG. 1 is inhibitory activity against VCAM-1 expression for group of HUVECs treated with tilianin, and strong inhibition against VCAM-1 expression was confirmed.

TABLE 3

| Classification | Control group | 10 μM tilianin group | 100 μM tilianin group |
|---|---|---|---|
| Mean intensity (Relative intensity) | 113 | 91 | 84 |
| Inhibition ratio of VCAM-1 expression (%) | — | 19.5 | 25.7 |

EXAMPLE 4

Inhibitory Activity Against NO Production

The process of experiment on inhibitory activity against NO production of mouse monocyte/macrophage cells RAW264.7 (RAW264.7 cells) whose activation is induced by lipopolysaccharide is as follows.

The experiment was carried out using the modified method of Sherman et al. (Sherman et. al., Biochem. Biophys. Res. Commun. 191, 1301-1308, 1993). The production of $NO_3$, a stable oxide of NO, and inhibition ratio of production by samples were measured for RAW264.7 cells. RAW264.7 cells were incubated in $CO_2$ incubator (5% $CO_2$, 95% relative humidity, 37° C.) for 48 hours after adding LPS (10 μg/ml) to RAW264.7 cells which were cultured in Dulbecco's Modified Eagle's medium (Gibco BRL, USA, 100 U/ml of penicillin and 100 μg/ml of streptomycin, 10% FBS, 6 g/L of HEPES, 3.7 g/L of $NaHCO_3$), and inducing activation. Then, 100 μl of Griess reagent (37.5 mM sulphanilic acid, 12.5 mM N-(1-naphthyl) ethylenediamine dihydrochloride, 6.5 mM hydrochloric acid) was added to the upper solution which was gained from centrifuging (1000 rpm, 10 minutes) the medium and it was incubated in room temperature for 10 minutes, and then the absorbance was measured by spectrophotometer at 540 nm. $NO_3$ concentration produced from RAW264.7 cells was calculated using the correlation coefficient of $NO_3$ concentration-absorbance drew up by nitrate prepared in 0~50 μM. Samples for test were melted in DMSO and added to RAW264.7 cells by 0.1% 2 hours prior to treatment of LPS, and then inhibition ratio of $NO_3$ production by samples was calculated by measuring $NO_3$ concentration after the reaction.

Standard equation of NO concentration =

$$\text{Absorbance}(540 \text{ nm}) \times 179.4215 - 8.5221$$

Inhibition ratio of NO production (%) =

$$\frac{\text{Mean value of NO concentration of sample group}}{\text{Mean value of NO concentration of lipid group}} \times 100$$

As a result, the high inhibitory activity against NO production was found in the extract of *Agastache rugosa*, the chloroform fraction, and n-butanol fraction, as shown in Table 4,

TABLE 4

| Sample | Treatment (μg/ml) | NO product (nM) | Inhibition rate of NO production (%) |
|---|---|---|---|
| Control | — | 4.35 ± 1.6 | — |
| LPS | — | 26.9 ± 4.2 | — |
| LPS + extract of | 50 | 17.1 ± 3.4 | 43.6* |
| *Agastache rugosa* | 100 | 13.7 ± 2.1 | 58.7* |
| LPS + n-hexane | 50 | 24.7 ± 7.9 | 9.8 |
| fraction | 100 | 13.7 ± 4.3 | 58.7* |
| LPS + chloroform | 50 | 14.0 ± 1.1 | 57.3** |
| fraction | 100 | 8.9 ± 3.4 | 80.0** |
| LPS + n-butanol | 50 | 24.2 ± 4.2 | 12.0 |
| fraction | 100 | 13.6 ± 0.2 | 59.1** |

**$P < 0.01$,
*$P < 0.05$

EXAMPLE 5

Anti-inflammatory Activity of Carrageenan-induced Acute Inflammation Model

Male Sprague-Dawley rats (210~220 g) were used as experimental animals, carrageenan was used as the inflammation agent, and inhibition ratio of edema against samples for test was investigated for edema-induced model. Following is the process of experiment.

200 mg/kg of the extract of *Agastache rugosa* suspended in water as sample for test was fed to each mouse and one hour later 0.1 ml of 1% carrageenan suspension in 0.85% saline was administrated under hypodermis near hind legs. Thickness of models' soles in 7 mice/group was measured every hour for 5 hours after administration. Wherein, thickness of models' soles in control (saline) group was measured together and inhibition ratio of edema of sample group was investigated according to increase of edema of control group dependent on time.

Inhibition ratio of edema (%) =

$$1 - \frac{\text{Mean value of increase of sole sickness in sample group}}{\text{Mean value of increase of sole thickness in control group}} \times 100$$

Table 5 indicates anti-inflammatory activity of the exacts of *Agastache rugosa* in carrageenan-induced acute inflammation model. The exacts of *Agastache rugosa* showed strong anti-inflammatory activity from 2 hours of administration, and the inhibition effect against edema lasted for 5 hours of measurement.

TABLE 5

| Sample | Time after treatment (hour) | Edema volume (%) | Inhibition rate of edema (%) |
|---|---|---|---|
| Extacts of | 0 | 100 | — |
| *Agastache rugosa* | 1 | 100 | — |
| (200 mg/kg, p.o.) | 2 | 45.8 | 54.2** |
| | 3 | 63.4 | 36.6* |
| | 4 | 60.8 | 39.2* |
| | 5 | 68.4 | 31.6* |

**$P < 0.01$,
*$P < 0.05$

EXAMPLE 6

Inhibitory Activity Against Atherosclerotic Lesion

The process of experiment on inhibitory activity of atherosclerotic lesion described in detail is as follows.

Step I) Mouse Breeding and Experiment on Administration of the Extract of *Agastache rugosa* to the Mouse Models for use, female LDLR−/−mice (6~8 weeks, average weight 16.8 g), were randomly divided into two groups of 10, respectively. One group was fed on a high cholesterol diet (15% fat, 1.25% cholesterol, 0.5% Na-cholate) and the other group was fed on the above diet mixed with supplement of 0.1% and 1% of sample for test. During the experiment, the mice had free access to water and food.

Step II) Measurement of Atherosclerotic Lesion Models

After 8 weeks of experiment, the blood was gathered through the eyes of all mice. Then, PBS (Phosphorus Buffer Solution) was flowed through the heart and the artery of mice for 10 minutes and subsequently paraformaldehyde was flowed through for 5 minutes. After this process, the heart and the artery were ripped off, immersed in 10% neutral formalin for 24 hours, embedded in OCT medium (10.24% poly vinyl alcohol, 4.26% poly ethylene glycol, 80.5% nonreactive ingredient, w/w, Life Science International, England, UK) and then kept at −70° C. Six frozen sections (9 μm each), prepared beginning from the area of artery using microtome maintaining low temperature (−20° C.), were stained with Oil red O and counter-stained with Harris hematoxylin. These stained sections were then quantified by computer-assisted morphometry and the average lesion size was calculated for each animal group. In this manner, inhibitory activity against sample group's lesion according to outbreak of control group's lesion was calculated.

Inhibition ratio of edema (%) =

$$1 - \frac{\text{Mean size of lesion of sample group}}{\text{Mean size of lesion of control group}} \times 100$$

(wherein, control group means high cholesterol diet group)

(1) The Result of Experiment on Inhibitory Activity Against Atherosclerotic Lesion in *Agastache rugosa* Group As shown in Table 6, there was no change in the amount of intake and weight in *Agastache rugosa* group for 8 weeks of experiment, compared to the control group.

TABLE 6

| | Weight (g) | | |
|---|---|---|---|
| Group of model | 0 week | 4 Weeks | 8 weeks |
| Control group | 16.8 ± 1.2 | 19.8 ± 1.4 | 21.1 ± 1.6 |
| 1% extract of *Agastache rugosa* group | 16.6 ± 1.1 | 19.7 ± 1.1 | 20.8 ± 1.8 |

Also, as shown in Table 7, the result of effect on inhibition against atherosclerotic lesion of the extract of *Agastache rugosa* indicates that the lesion size of the group fed on a diet including 0.1% and 1% extracts of *Agastache rugosa* was decreased by 23% and 46.6%, respectively, compared to the control group.

TABLE 7

| Sample | Concentration (%) | Lesion size (μm²) | Inhibitory activity (%) |
|---|---|---|---|
| Control group | — | 304644.0 ± 76602.6 | — |
| Extract of Agastache rugosa group | 0.1 | 232120.3 ± 32534.04 | 23.8 |
|  | 1.0 | 162629.6 ± 28362.1 | 46.6* |

*P < 0.01

Figure 2:
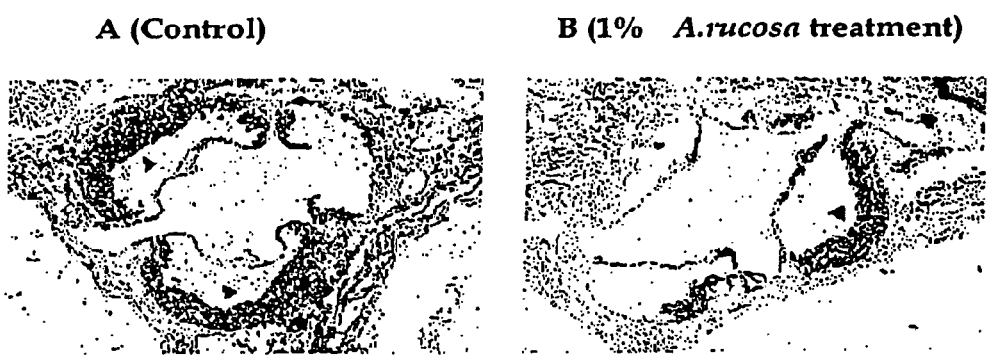
FIG. 2 shows effect of Agastache rucosa extract on atherosclerotic lesions in Oil red O-stained aortic valve lesion areas of Ldlr−/−mice fed with a cholesterol diet for 8 weeks. Representative cross-sections of aortic valves (×100) in hearts from (A) control group and (B) 1% Agastache rucosa extract-diet group.
Figure 3:
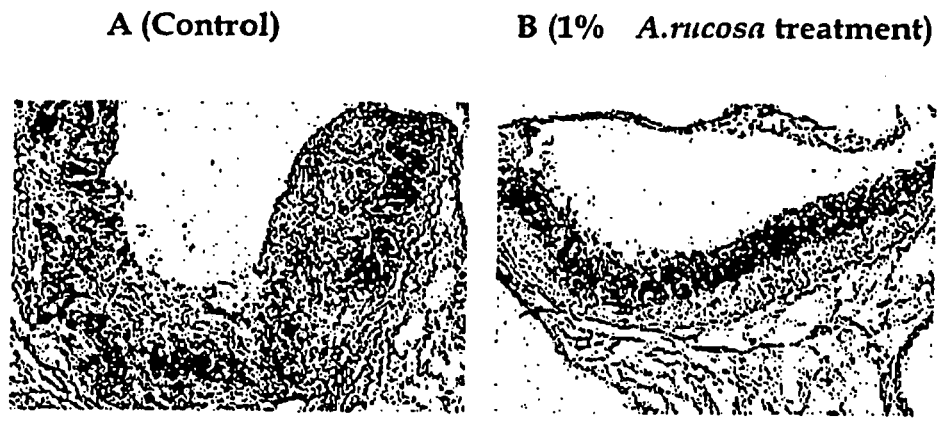
FIG. 3 shows immunochemical staining of the macrophage accumulation of aortic valve lesions (×100) from (A) control group and (B) 1% Agastache rucosa extract-diet group in the Ldlr−/−mice fed with a cholesterol diet for 8 weeks by using the monoclonal antibody to mouse macrophages-2 (MOMA-2, Serotec Inc. NC. USA).

And, when the cross-section of artery of heart was stained, the lesion (necrotic tissue) size due to inflammation showed a significant decrease in the group of 1% extract of *Agastache rugosa* compared to the control group (FIG. 2). And, when just macrophages of the lesion were stained, accumulation of macrophages showed a significant decrease in the group of 1% extract of *Agastache rugosa* compared to the control group (FIG. 3).

Therefore, the progress of atherosclerotic lesion growing into accumulation and inflammation of immunocytes such as macrophages under endothelial cells shows that the extract of *Agastache rugosa* decreases significantly the development of the lesion due to inflammation.

(2) The Result of Experiment on Inhibitory Activity Against Atherosclerotic Lesions in Tilianin Group As shown in Table 8, the result of effect on inhibition against atherosclerotic lesion of tilianin indicates that the lesion size of the group fed on a diet including 1% tilianin was decreased by 41.9% compared to the control group.

TABLE 8

| Sample | Concentration (%) | Lesion size (μm²) | Inhibitory activity (%) |
|---|---|---|---|
| Control group | — | 592981.4 ± 98784.2 | — |
| Tilianin | 1.0 | 344277.7 ± 186833.8 | 41.9** |
| Lovastatin* | 1.0 | 291442.0 ± 96927.8 | 50.9*** |

*positive control,
**P < 0.003,
***P < 0.0002

As shown in Table 8, inhibitory activity against atherosclerotic lesion in 1% lovastatin group was higher than in 1% tilianin group, but tilianin according to the present invention is safe: with no side effect while lovastatin has a toxic effect on liver. Also, it was ascertained that the tilianin group according to the present invention is much more effective than the control group.

Figure 4:
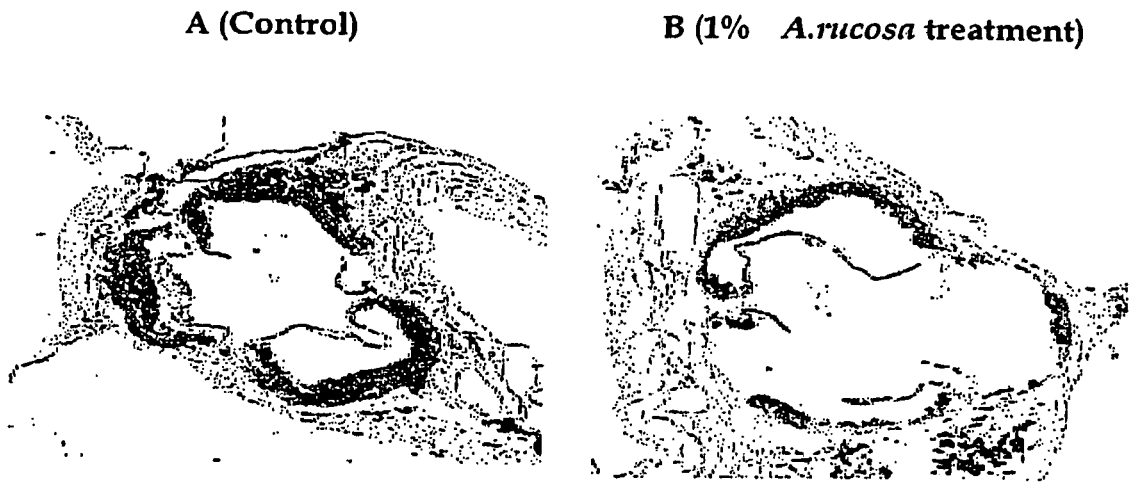
FIG. 4 shows effect of tilianin on atherosclerotic lesions in aortic valve lesion areas of Ldlr−/−mice fed with a cholesterol diet for 8 weeks. Representative cross-sections of aortic valves (×40) in hearts from (A) control group and (B) 1% *Agastache rucosa* extract-diet group.

And, the result of staining cross-section of artery of heart showed that the lesion (necrotic tissue) size caused by the inflammatory response was decreased significantly in the 1% tilianin group compared to the control group (FIG. 4). Therefore, in the progress of atherosclerotic lesion groping into accumulation and inflammation of immunocytes such as macrophages under endothelial cells, tilianin was confirmed to decrease the development of atherosclerotic lesion significantly.

EXAMPLE 7

Preparation of Tablets

Tablets were prepared by the direct tableting method after crushing and mixing 10 g of the extract of *Agastache rugosa* (including 1 g of tilianin), 70 g of lactose, 15 g of crystalline cellulose and 5 g of magnesium stearate. The total amount of each tablet was 100 mg and the amount of extract of *Agastache rugosa* as an active ingredient was 10 mg (1 mg of tilianin).

EXAMPLE 8

Preparation of Powders

Powder was prepared by crushing and mixing 10 g of the extract of *Agastache rugosa* (including 1 g of tilianin), 50 g of corn starch and 40 g of carboxycellulose. And capsules were prepared by putting 100 mg of powder into capsules with hardness VI.

EXAMPLE 9

Test of Toxicity

From the old times, the extract of *Agastache rugosa* and tilianin obtained by separation-purification were nontoxic materials and natural medicines used as foods and medicines. 1 g/kg of component dissolved in dimethylsulfoxide (DMSO) and diluted in water was administrated to each mouse (10 mice/group) and no mouse was found dead after 7 days.

EXAMPLE 10

Ingredient for Drink Including the Extract *Agastache rugosa*

Plum extract (plum solid extract (solids amount 69° Bx), maker: Hadong National Agricultural Cooperative Federation in Korea), a Chinese quince, a *Angelica gigas* Nakai, a dried ginger, *Maximowiczia chinensis*, a cinnamon (Kyongdong Market, Seoul), grape juice (solids amount 65° Bx, maker: Comax international Corp.), and pear juice (maker: Hanmi aromatics chemistry) were prepared as ingredients for drink including the extract of *Agastache rugosa*.

First, natural medicines such as a Chinese quince, a *Angelica gigas* Nakai, a dried ginger, a *Maximowiczia chinensis*, and a cinnamon were hydrothermally extracted at 100° C. for 30 minutes after adding water of ten times the weight of each natural medicine. These were kept at 4° C. for 24 hours and after centrifuging them for 10 minutes, the extract of a natural medicine from the upper solution was used.

Also, the plum extract was used with the plum solid extract (69° Bx) diluted to 10° Bx, the grape juice (65Bx °), and pear juice (69Bx °) were used as undiluted.

For ingredients for drink including the extract of *Agastache rugosa*, 0.1% extract of *Agastache rugosa*, 0.2% plum extract, 0.3% the extract of dried ginger, 0.3% the extract of Chinese quince, 0.01% the extract of cinnamon, 5.0% pear juice, and 17% superfructose were diluted in water to set to 100 ml, irradiated and treated at 95° C. for 15 seconds to prepare goods of drink type.

In the above is mentioned about the method of preparing the goods of drink type including the extract of *Agastache rugosa*, but the drinkable goods for health including tilianin instead of the extract of *Agastache rugosa* with the same purpose could be prepared.

As mentioned above, the extract of *Agastache rugosa* and tilianin obtained by separation-purification according to the present invention inhibit activation, production, and expression of various inflammatory factors, have the anti-inflammatory activity in animals and significant inhibitory activity against production of atherosclerotic lesion, therefore, they are useful as drugs or food additives for preventing or treating inflammatory diseases, atherosclerosis which is related to inflammatory responses and a disease of circulatory system due to atherosclerosis.

What is claimed is:

1. A method of treating atherosclerosis in a mammal, comprising administering to a mammal in need, a therapeutically effective amount of an extract of *Agastache rugosa*.

2. A method according to claim 1, wherein administration amount of the extract of *Agastache rugosa* is from 0.1 to 100 mg/kg.

3. A method according to claim 1, wherein the extract contains tilianin as an active ingredient.

4. A method according to claim 3, wherein administration amount of the tilianin is from 0.1 to 100 mg/kg.

5. A method according to any of claims 1-4, wherein the extract contains a solvent fraction fractionated by n-hexane, chloroform, or n-butanol.

6. A method according to any of claims 1-4 wherein said mammal is human.

7. A method according to claim 5, wherein said mammal is human.

8. A method of treating atherosclerosis in a mammal, consisting essentially of administering to a mammal in need, a therapeutically effective amount of an extract of *Agastache rugosa*.

9. A method according to claim 8, wherein administration amount of the extract of *Agastache rugosa* is from 0.1 to 100 mg/kg.

10. A method according to claim 8, wherein the extract contains tilianin as an active ingredient.

11. A method according to claim 10, wherein administration amount of the tilianin is from 0.1 to 100 mg/kg.

12. A method according to any of claims 8-11, wherein the extract contains a solvent fraction fractionated by n-hexane, chloroform, or n-butanol.

13. A method according to any of claims 8-11, wherein said mammal is human.

14. A method according to claim 12, wherein said mammal is human.

* * * * *